United States Patent

Butler et al.

Patent Number: 6,137,020
Date of Patent: Oct. 24, 2000

[54] ALKYLATION PROCESS WITH REDUCED HEAVY RESIDUE

[75] Inventors: James R. Butler, Houston; Mark E. Kuchenmeister, Friendswood, both of Tex.

[73] Assignee: Fina Technology, Inc., Houston, Tex.

[21] Appl. No.: 09/127,025

[22] Filed: Jul. 31, 1998

Related U.S. Application Data

[63] Continuation-in-part of application No. 08/503,660, Jul. 17, 1996, abandoned, which is a continuation-in-part of application No. 08/407,222, Mar. 21, 1995, abandoned.

[51] Int. Cl.$^7$ .................................................. C07C 15/067
[52] U.S. Cl. ........................ 585/446; 585/453; 585/455; 585/457; 585/467; 585/470; 585/474; 585/475
[58] Field of Search .................................. 585/446, 453, 585/455, 457, 467, 470, 474, 475

[56] References Cited

U.S. PATENT DOCUMENTS

| | | | |
|---|---|---|---|
| 4,070,407 | 1/1978 | Haag et al. | 585/467 |
| 4,490,570 | 12/1984 | Forward et al. | 585/467 |
| 4,520,220 | 5/1985 | Watson et al. | 585/467 |
| 4,599,473 | 7/1986 | Debras et al. | 585/467 |
| 5,177,280 | 1/1993 | Juguin et al. | 585/323 |
| 5,248,841 | 9/1993 | Young | 585/467 |
| 5,847,255 | 12/1998 | Ghosh et al. | 585/467 |

*Primary Examiner*—Elizabeth D. Wood
*Attorney, Agent, or Firm*—William D. Jackson; Jim D. Wheelington

[57] ABSTRACT

A process for reducing the amount of undesirable byproducts, for example multi-ring compounds known as heavy residue in a process for the alkylation of an aromatic hydrocarbon with an olefin using a silicalite catalyst is disclosed. The process comprises supplying a feedstock containing benzene to a reaction zone with an alkylating agent in a molar ratio of benzene to alkylating agent of from about 2:1 to about 20:1 and into contact with an aluminosilicate alkylation catalyst having an average crystallite size of less than about 0.50 μm and wherein the size of about 90% of the crystallites is less than 0.70 μm. The catalyst is characterized by an Si/Al atomic ratio in the range from between 50 and 150 and a maximum pore size in the range from about 1000 to 1800 Å. The catalyst has a sodium content of less than about 50 ppm and the reaction is carried out under conversion conditions including a temperature of from about 250° C. to about 550° C. and a pressure of from about 200 psi to about 500 psi.

23 Claims, 5 Drawing Sheets

ALKYLATION PROCESS WITH REDUCED HEAVY RESIDUE

CROSS REFERENCE TO RELATED APPLICATIONS

This application is a continuation-in-part of application Ser. No. 08/503,660, filed Jul. 17, 1996, now abandoned, which is, in turn, a continuation in part of application Ser. No. 08/407,222, filed Mar. 21, 1995, now abandoned.

TECHNICAL FIELD

The present invention relates to a process for reducing the amount of undesirable byproducts, for example multi-ring compounds known as heavy residue, resulting from the alkylation of aromatic feedstock with an alkylating agent using an aluminosilicate catalyst having an Si/Al atomic ratio of at least 50.

BACKGROUND OF THE INVENTION

Ethylbenzene is used primarily for the production of styrene monomer obtained through dehydrogenation. Currently, much of the ethylbenzene produced is obtained by alkylation of benzene with ethylene under a variety of alkylation conditions. One type of alkylation process involves vapor phase reactions in which benzene is alkylated with an olefin such as ethylene under high temperatures and pressures over an aluminosilicate catalyst in a multiple bed reactor.

A significant problem in the production of ethylbenzene by alkylation of benzene with ethylene under high temperatures and pressures is the production of undesired byproducts, including polyalkylbenzenes such as polyethylbenzenes (PEB's) and multi-ring compounds known collectively as "heavy residue". Although the production of PEB's and heavy residue may be limited to some extent by supplying a stoichiometric excess of benzene to the reactor, significant quantities of these materials are nevertheless generated during the alkylation process.

In conventional vapor phase alkylation of benzene with ethylene, the reactor effluent is subjected to successive fractionations to separate benzene, ethylbenzene, PEB's and heavy residue to separate streams. The PEB stream may be directed to a separate transalkylation reactor or recycled to the alkylation reactor.

In the case where the PEB stream is recycled to the alkylation reactor, the recycled PEB stream can constitute up to ten percent of the total feed to the alkylation reactor. Consequently, if the transalkylation activity of the catalyst is not sufficient to control the concentration of PEB's in the alkylation reactor effluent, the volume of recycled PEB's will increase and eventually become too large to manage within process capacity. Therefore, it is important that the catalyst used in the alkylation of benzene with ethylene in a process with PEB recycle to the alkylation reactor have sufficient transalkylation activity to convert recycled polyalkylbenzenes at a rate sufficient to maintain the volume of the recycled polyalkylbenzenes stream at a level within process capacity.

A bottom stream of heavy residue is withdrawn from the reactor and usually burned as fuel. The residue is typically comprised of multi-ring compounds such as naphthalenes and diphenylethanes and has little commercial value. If not removed, this heavy residue will build up in the reactor stream, eventually overwhelming the ethylbenzene production process. This residue represents a loss of raw materials, since it is useful only as fuel, decreasing the profitability of the alkylation process. This purge stream has heretofore represented about one weight percent of the output of the alkylation process based on the weight of ethylbenzene produced.

In connection with the foregoing, it has been discovered that the use of a silicalite alkylation catalyst having a crystallite size within a specified range results in increased transalkylation activity, allowing for greater control of the volume of recycled alkylbenzenes in the process. In addition, an alkylation process has been discovered that minimizes the amount of heavy residue produced in alkylation/transalkylation of aromatic hydrocarbons.

SUMMARY OF THE INVENTION

The present invention provides a method for transalkylating polyalkylbenzenes that is particularly useful in an alkylation process in which benzene is reacted with ethylene to produce ethylbenzene under reaction conditions. The process of the present invention provides greater control of the amount of polyalkylbenzenes recycled in such a process, resulting in increased ability to maintain an acceptable level of recycled polyalkylbenzenes. Also disclosed is a method for decreasing the amount of heavy residue produced during the alkylation process that must be discarded as a purge stream.

The processes comprise supplying a feedstock containing benzene and recycled polyalkylbenzenes into a reaction zone with an alkylating agent in a molar ratio of benzene to alkylating agent of from about 2:1 to about 20:1 and into contact with an aluminosilicate alkylation catalyst having an Si/Al atomic ratio of at least 50 and a maximum average crystallite size of about 0.5 $\mu$m (0.5 microns).

In one embodiment of the present invention, the catalyst comprises predominantly monoclinic silicalite formulated with refractory oxide binder, preferably alumina. About 90% of the catalyst crystallites are less than 0.7 $\mu$m in size. The catalyst is further characterized by an Si/Al atomic ratio in the range from between 50 and 500 and a maximum average pore size of the refractory oxide binder in the range of about 1000 to 4000 Å, preferably about 1000 to 1800 Å. The silicalite catalyst has a sodium content of less than about 50 ppm and the reaction is carried out under conversion conditions including a temperature of from about 250° C. to about 500° C. and a pressure of from about 200 psi to about 500 psi.

An effluent stream containing ethylbenzene is recovered from the reaction zone. A purge stream comprising heavy residue is separated and withdrawn in one embodiment of the present invention. A process of the present invention minimizes the amount of heavy residue that must be purged from the alkylation process.

In carrying out the present invention, a mixture of an aromatic hydrocarbon and an alkylating agent is reacted in an alkylation zone containing an alumosilicate molecular sieve catalyst of predominantly monoclinic symmetry. The molecular sieve catalyst has an Si/Al atomic ratio of 50–500 and an average crystallite size of no more than about 0.5 microns. The alkylation zone is operated under conversion conditions to produce an alkylated aromatic hydrocarbon stream. Unreacted aromatic hydrocarbon is separated from the alkylated aromatic hydrocarbon stream. Alkylated aromatic hydrocarbon is recovered from the alkylated aromatic hydrocarbon stream to leave a remainder stream. This remainder stream is separated into a first residual hydrocarbon stream and a second residual hydrocarbon stream which contains less than 0.8 wt. % of the alkylated hydrocarbon stream based on the weight of the alkylated aromatic hydrocarbon. This second residual stream is purged from the process. Preferably, the second residual hydrocarbon stream which is purged from the process contains less than 0.5 wt. % of the alkylated aromatic stream based on the weight of the alkylated aromatic hydrocarbon.

In a further aspect of the invention, the first residual hydrocarbon stream is subject to a transalkylation step. In one embodiment of the invention, the transalkylation step takes place in the alkylation zone. In another embodiment the transalkylation step takes place in a separate transalkylation unit. In a preferred embodiment of the invention the molecular sieve catalyst is of a particle size distribution in which 90% of the crystallites of the catalyst is less than 0.70 microns. In a further aspect of the invention, the catalyst is configured with a binder to provide a maximum pore size within the range of about 1,000–4,000 angstroms and, more preferably, within the range of about 1,000–1,800 angstroms.

DETAILED DESCRIPTION OF THE INVENTION

The process of the present invention can be carried out using a variety of process equipment, including a reactor vessel which defines a reaction zone containing catalyst material. Either single or multiple catalyst beds can be employed in the reaction zone. The ethylene and benzene reactants may be mixed and preheated prior to introduction to the reaction zone which may consist of one or more catalyst beds where the reactants contact the catalyst under reaction conditions. The reaction products are withdrawn from the reaction zone after a controlled residence time and the reaction products are collected and separated by conventional techniques. Excess benzene, along with polyalkylbenzenes, are typically recycled to the reaction zone. The heavy residue is withdrawn as a purge stream and typically disposed of or used as a fuel.

Figure 1:
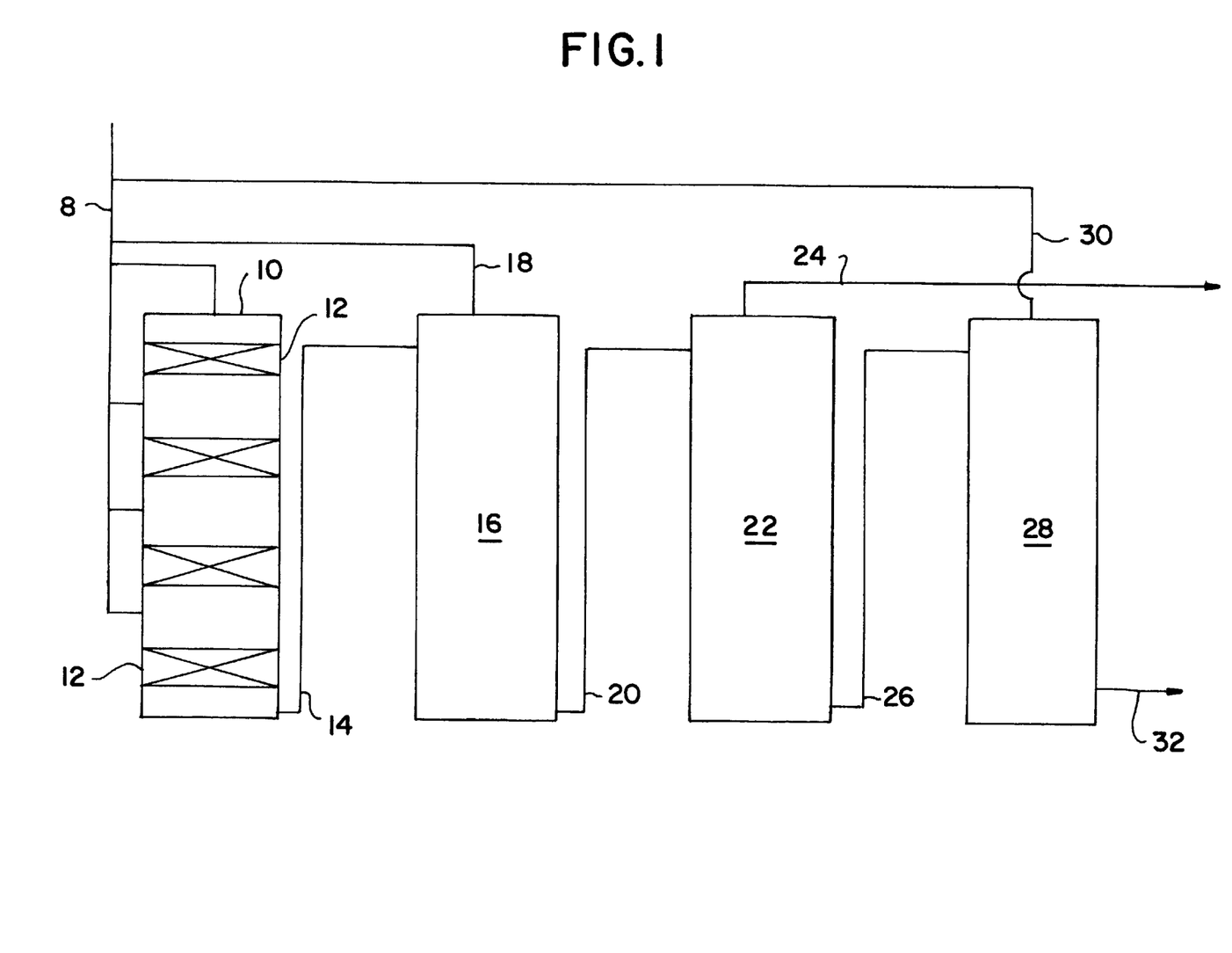
FIG. 1 is a schematic illustration of a process embodying the present invention.

Turning now to FIG. 1, one embodiment of the process of the present invention is schematically illustrated. A feed stream 8 containing benzene and an alkylating agent such as ethylene is injected into a multiple bed alkylation reactor 10 where the reactants are brought into contact with a catalyst in catalyst zones 12. Since the alkylation reaction is highly exothermic, the reactants may be injected at multiple locations in the reactor for process control purposes. An effluent stream 14 from the reactor 10 is directed to one or more benzene fractionating columns 16 where benzene is separated from the reactor effluent. The overhead stream 18 from the benzene fractionating column is recycled to the feed stream 8 to the alkylation Reactor 10. The bottom stream 20 from the benzene fractionating column 16 is directed to an ethylbenzene fractionating column 22 where an ethylbenzene product stream 24 is separated and recovered. The bottom stream 26 from the ethylbenzene fractionating column 22 is directed to a third fractionating column 28 where an overhead stream 30 containing PEB's is separated and recycled to the alkylation reactor 10. In addition to PEB's, the overhead stream 30 may contain varying amounts of lower boiling point compounds such as xylenes, styrene, cumene, and propylbenzene.

Higher boiling point residual materials are recovered as the bottom stream 32 from the third fractionating column 28 as heavy residue. This purge stream, containing, multi-ring compounds such as napthalenes and polyphenyl ethanes, is disposed of or burned as fuel.

The catalyst used in the process of the present invention is selective to the production of ethylbenzene in a temperature range of from about 250° C. to about 500° C. and a pressure range of from about 200 psi to about 500 psi. The catalyst is an aluminosilicate powder with a crystalline structure that is primarily monoclinic silicalite, but which may contain up to about 40% orthorhombic crystalline structure. In one embodiment of the present invention, the catalyst contains about 20 weight percent alumina binder. Importantly, the catalyst has sufficient transalkylation activity to convert an amount of the recycled polyalkylbenzenes sufficient to maintain the volume of the recycled polyalkylbenzene stream at a level within conventional process capabilities. It has been further discovered that the catalyst may be used in a process to reduce the amount of residue that must be purged from the alkylation process.

The Si/Al atomic ratio of the catalyst is preferably in the range of from about 50 to about 500, more preferably in the range of from about 50 to 150 and even more preferably in the range of from about 70 to about 130 for enhanced transalkylation. As used herein the Si/Al ratio refers to the atomic ratio of silicon to aluminum in the catalyst to the exclusion of the binder.

Figure 2:
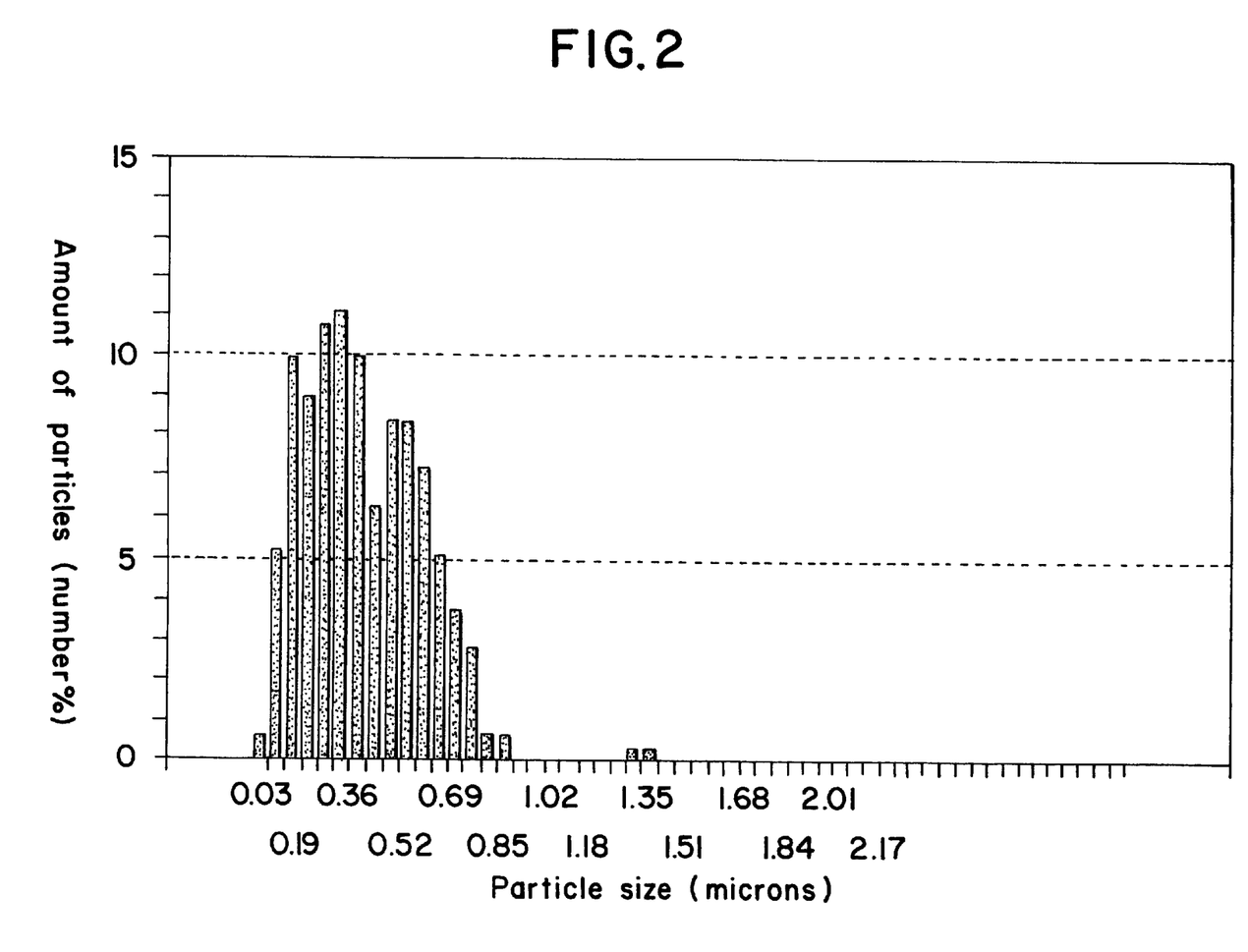
FIG. 2 is a graphical illustration of the size distribution of the crystallites of the catalyst used in the practice of the present invention.

As is well known in the art, aluminosilicate alkylation catalysts, commonly referred to as "molecular sieves" because of their shape-selective characteristics, can be prepared by the hydrothermal digestion of a reaction mixture comprising silica and water in the presence of a organic templating agent. Various other components may also be present. For example, ZSM-5-type zeolites can be prepared by the hydrothermal digestion of a reaction mixture comprising silica, alumina, sodium or another alkyl metal oxide and a templating agent, such as a tetra alkyl ammonium halide. Aluminosilicate molecular sieves of relatively high silica/alumino ratio of monoclinic symmetry, commonly denominated as "silicalite," can be prepared from similar reaction mixtures except that alumina is not usually intentionally added as part of the reaction mixture. Unless steps are taken to convert the silicalite molecular sieves to monoclinic symmetry, they, like their ZSM-5 counterparts, are of orthorhombic symmetry. Basic procedures for preparing silicalite molecular sieves are disclosed in U.S. Pat. No. 4,061,724 to Grose et al. As disclosed there, a suitable reaction mixture can be prepared from a mixture of relatively minor amounts of sodium hydroxide in water to which is added an aqueous dispersion of colloidal silica sol. Thereafter, a suitable templating agent can be added to form the reaction mixture which is then digested under suitable time and temperature conditions—for example, heating at 200° C. under pressure for three days, followed by calcination for a relatively short period of time in order to remove the templating agent. As readily understood by those skilled in the art, the templating agent and the reaction conditions can be selected to control crystal size and morphology of the molecular sieve. Among the templating agents disclosed in Grose et al are tetraethylammoniumhydroxide, tetrapropylammonium hydroxide,tetrabutylammonium hydroxide, tetrabutylphosphonium hydroxide, and the corresponding halides, specifically the corresponding chloride, iodide, and bromide salts. As noted previously, while in Grose et al the silicalite produced there is of orthorhombic symmetry, it is well known in the art to produce silicalite molecular sieves of monoclinic symmetry. For a further description of synthesis procedures for the preparation of high silica alumina ratios of controlled morphology by hydrothermal synthesis reference is made to the aforementioned patent to Grose et al and also the Flanigen et al, "Silicalite, a new hydrophobic crystalline silica molecular sieve," *Nature*, Vol. 271, Feb. 9, 1978, pp. 512–516, the entire disclosures of which are incorporated by reference. The improvement in transalkylation control and residue production of the processes of the present inventions are attributed to the use of a silicalite catalyst having an average crystallite size of about 0.5 $\mu$m (0.5 microns) or less. In addition to the small crystallite size of the catalyst, the size distribution of the crystallites is also narrow. As illustrated in FIG. 2, the average crystallite size of the catalyst is less than about 0.5 $\mu$m, with approximately 90% of the crystallites having a size less than 0.70 $\mu$m. Catalysts with average crystallite sizes exceeding the specified maximum average size of about 0.50 $\mu$m have proven to have lower transalkylation activity and therefore afford less control of the volume of polyalkylbenzenes recycled in the process.

Figure 3:
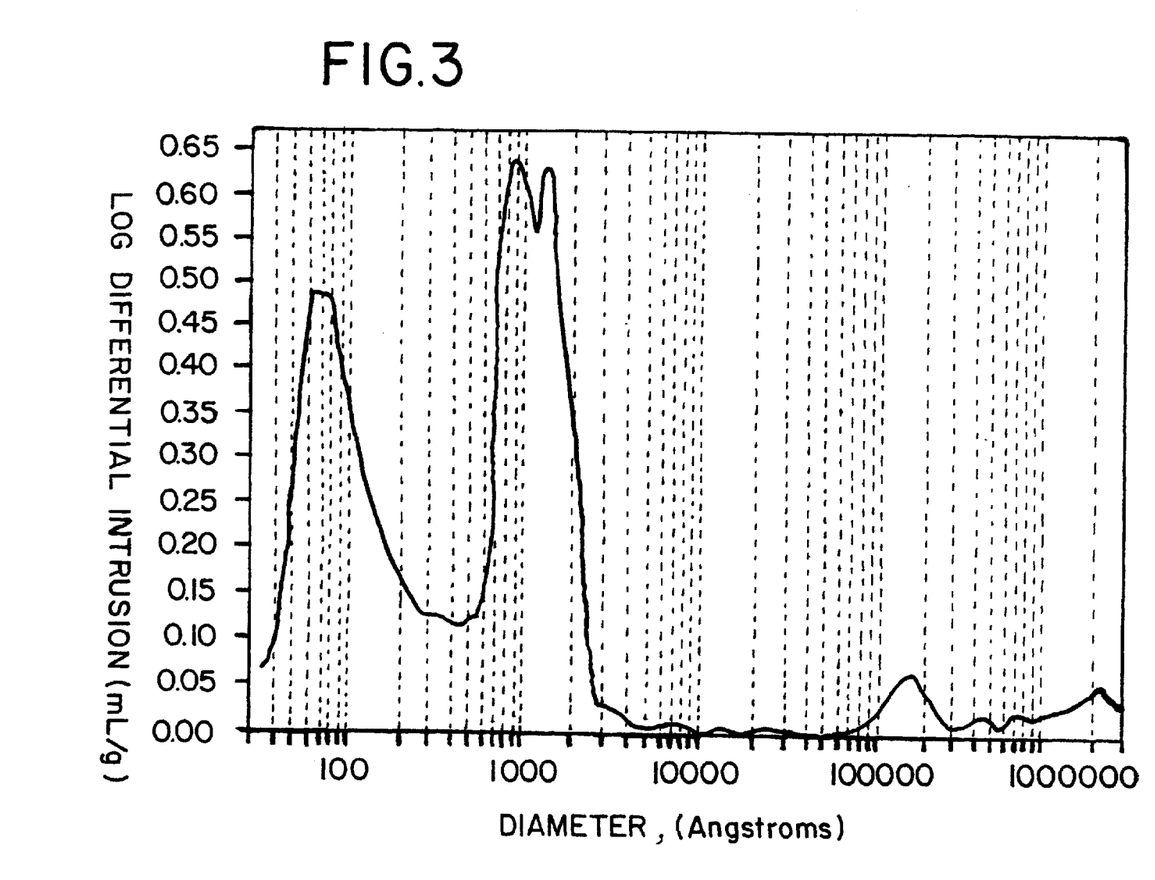
FIG. 3 is a graphical illustration of the distribution of pore sizes of the catalyst used in the practice of the present invention.

The pore size characteristics of the catalyst are also significant. As will be understood by those skilled in the art, molecular sieve catalysts which are particularized with a binder, such as alumina, can be characterized in terms of two pore sizes. The smaller pore size is the average pore size of the molecular sieve crystals and is important in imparting shape selectivity to the molecular sieve. This smaller pore size diameter is on the order of a few angstroms, about 5–6 angstroms in the case of the preferred silicalite catalyst employed in the present invention. The second pore size which is much larger, and thus referred to as the maximum pore size or simply the binder pore size, is the average pore size of the refractory oxide binder, such as the alumina binder employed in particularizing the silicalite catalyst used in the present invention. Both pore sizes are significant as is the crystallite size of the silicalite molecular sieve itself. Here, however, the refractory oxide binder has a somewhat larger pore size than is associated with binders commonly used to form molecular sieve catalyst particles. The relatively large maximum pore size of the particularized silicalite used in the present invention is significant in avoiding, or at least minimizing a limiting diffusion mechanism as applied to the catalyst particles themselves which, as noted previously, typically can contain about 20 wt. % of the binder. Preferably, the maximum pore size ranges from about 1000 Å (1000 Angstroms) to about 1800 Å. FIG. 3 illustrates the maximum pore size distribution by volume for a catalyst used in the practice of the present invention. Additionally, the sodium content of the catalyst should be maintained at a level less than about 50 ppm in order to facilitate the desired levels of transalkylation and to minimize residue production.

The silicalite employed in the present invention, in addition to having a relative high silica/alumina ratio, has a somewhat smaller crystal size than the silicalite traditionally employed in aromatic alkylation procedures. As noted above, silicalite, as is well known in the art, is a molecular sieve catalyst which is similar to the ZSM-5 zeolites but is typically characterized by a higher silica/alumina ratio providing an aluminum unit cell ratio of less than 1, and, in addition, is normally characterized as having a somewhat larger than average crystal size than is commonly associated with the ZSM zeolites. As noted above, silicalite, which in the as-synthesized form following the Grose et al synthesis is characterized by orthorhombic symmetry, can be converted to monoclinic symmetry by a calcination procedure as disclosed, for example, in U.S. Pat. No. 4,599,473 to DeBras et al, the entire disclosure of which is incorporate herein by reference. As described in detail in DeBras et al, "Physico-chemical characterization of pentasil type materials, I. Precursors and calcined zeolites, and II. Thermal analysis of the precursors," *Zeolites*, 1985, Vol. 5, pp. 369–383, the entire disclosure of which is incorporated herein by reference, silicalite and other pentasil-type aluminosilicate molecular sieves can be varied in crystal size by the synthesis procedure and the composition of the reaction mixture, normally have a relatively large crystal size. Thus, at an average of less than one aluminum atom per unit cell (a silica/alumina ratio of about 200), the silicalite disclosed in the Debras et al paper typically has an average crystal size of perhaps 5–10 microns or more. U.S. Pat. No. 4,489,214 to Butler et al discloses experimental work involving the ethylation of toluene over silicalite of a somewhat smaller crystal size but still greater than one micron, ranging from 1–2 microns up to 8 microns. The silicalite is further characterized in terms of a variable aluminum gradient such that the aluminum gradient is positive when going from the interior to the surface of the molecular sieve crystal. That is, the silicalite can be characterized by a core portion which is relatively aluminum deficient with an outer shell portion which is relatively aluminum rich. It is to be understood that the term "aluminum rich" is a relative term and that for silicalite, even the outer shell portion of the crystallite has a low aluminum content.

The aluminosilicate alkylation catalysts employed in the present invention can be characterized generally as molecular sieves from the pentasil family of high silica molecular sieves. Such pentasil molecular sieves are described, for example, in Kokotailo et al, "Pentasil Family of High Silica Crystalline Materials," Chem. Soc. Special Publ. 33, 133–139 (1980). As noted previously, the silicalite aluminosilicate catalyst has an effective pore size or window within the range of 5–6 angstroms. The aluminosilicate catalyst has a somewhat smaller crystal size than is usually the case. As noted above, the maximum average crystal size is about 0.5 $\mu$, as contrasted with a crystal size of perhaps 1–2 $\mu$up to about 8 microns for the traditional silicalite catalysts such as disclosed in the aforementioned U.S. Pat. No. 4,489,214 to Butler et al.

A preferred silicalite for use in the present invention is extruded with an alumina binder in a "trilobe" shape having a nominal diameter of about $\frac{1}{16}$" and a length of the extrudate of about ⅛–¼". The "trilobe" cross sectional shape is something on the order of a three leaf clover. The purpose of this shape is to increase the surface area of the extruded catalyst beyond what one would expect with a normal cylindrical extrudate. The silicalite catalyst is predominately of monoclinic symmetry as described previously. Monoclinic silicalite may be prepared as disclosed in U.S. Pat. No. 4,781,906 to Cahen et al and U.S. Pat. No. 4,772,456 to DeClippeleir et al. Desirably, the catalysts will have high, near 100%, monoclinicity although silicalite catalysts that are 60–80% monoclinic and about 20–40% orthorhombic symmetry may be used in the preferred embodiment of the invention. The silicalite typically is present in an amount of about 80 wt. %, with the alumina binder being present in an amount of about 20 wt. %. The silica/alumina ratio of the silicalite is at least 100 and preferably at least 140 or stated in terms of the Si/Al atomic ratio at least 50 and preferably 70. An especially preferred silica/alumina ratio is about 225–350, and silicalite within this range was used in the experimental work described below. The silicalite may have an alpha value of about 20–30. The "alpha value" is characterized in terms of the activity of a catalyst for cracking hexane as disclosed in U.S. Pat. No. 4,284,529 to Shihabi and U.S. Pat. No. 559,314 to Shihabi. The catalyst typically contains small amounts of sodium and iron.

As noted previously, the silicalite alkylation catalyst has a crystal structure characterized by an aluminum rich outer shell and an aluminum deficient interior portion when compared with the outer shell. The silicalite catalyst is dry and has no appreciable or intended water content. The alumni binder is a high purity alumina such as "catapal alumina." The silicalite catalyst preferably contains only a small amount of sodium, typically 50 ppm sodium or less, and contains only a small amount of iron oxide, about 300–600 ppm. The catalyst need not contain any additional "promoter" metals incorporated during the synthesis of the catalyst.

The silicalite catalyst employed in the following experimental work was a predominantly monoclinic silicalite having a silica/alumina ratio of about 225–230. This catalyst was extruded with an alumina binder (about 20 wt. %) in a trilobe configuration as described above. The catalyst had an average crystal size of about 0.4 micron with a maximum average pore size, as determined by the binder, within the range of 1000–4000 Å. Another silicalite catalyst showing similar results was similar in crystal size and binder configuration but had a somewhat higher silica/alumina ratio of about 320. This is also predominantly monoclinic silicalite.

In the processes of the present inventions, an excess of benzene to ethylene is normally maintained in the feed to the reactor, typically in the range of from about 2:1 to 20:1 moles benzene to ethylene, preferably between about 3:1 to 16:1. Weight hourly space velocities are preferably in the range from about 20 to 150. Although reaction conditions employing temperature from about 250° C. to about 500° C. may be utilized, more preferably the reaction is conducted within a range of from about 300° C. to about 475° C.

The processes of the present inventions may be further illustrated by the following examples which are not to be construed as limiting the scope of the inventions as hereinafter claimed.

EXAMPLE 1

Ten milliliters of a aluminosilicate catalyst with mesh size between 20 and 40 mesh is introduced into a laboratory scale reactor. The catalyst has a crystallinity in the range of 76 to 93%, 64% monoclinicity, an average crystallite size of 0.41 μm, a maximum pore volume at a pore size of 1763 Å and an Si/Al atomic ratio of 114. The catalyst is heated under nitrogen flow to 150° C. overnight at ambient pressure to dry the catalyst. The temperature is increased to 200° C. and benzene with 10% mixed polyethylbenzenes is introduced to the reactor at a rate of 11.6 ml./min. The pressure is increased to 300 psig and the temperature raised to 400° C. After the temperature across the reactor bed has stabilized, the ethylene is introduced at a rate of 1 mole per 10 moles of benzene feed. The test is run for 15 days without interruption. During the test, diethylbenzene (DEB's) concentrations in the feed and effluent from the reactor are measured and the percentage of diethylbenzenes converted, based on the DEB concentration in the feed, is calculated. The ethylene feed is shut off periodically to determine the intrinsic diethylbenzene conversion rate. The results are set forth in Table 1 below:

TABLE 1

| Text Duration (days) | % DEB's Converted | % DEB's Converted Without Ethylene Feed |
| --- | --- | --- |
| 1.0 | 11.0 | 21.8 |
| 1.6 | 8.2 | — |
| 2.0 | 9.2 | 21.2 |
| 2.7 | 9.0 | — |
| 3.7 | 7.6 | — |
| 4.6 | 8.7 | 19.2 |
| 5.0 | 7.7 | — |
| 5.6 | 7.4 | — |
| 6.0 | 6.6 | — |
| 6.6 | 7.4 | — |
| 7.0 | 6.8 | — |
| 7.6 | 4.7 | 18.3 |
| 8.6 | 5.4 | — |
| 9.0 | 4.5 | — |
| 9.7 | 5.6 | — |
| 10.8 | 5.0 | — |
| 11.6 | 5.0 | 15.4 |
| 12.0 | 3.8 | — |
| 12.6 | 3.7 | — |
| 12.9 | 1.1 | — |
| 14.0 | 3.6 | 16.5 |
| 14.6 | 2.8 | 16.2 |

The foregoing example illustrates the substantial transalkylation activity afforded by the use of an aluminosilicate catalyst having a crystallite size in accord with the process of the present invention. The following Comparative Example will further illustrate the advantages of the process of the present invention.

COMPARATIVE EXAMPLE 1

Ten milliliters of an aluminosilicate catalyst having a mesh size of from 20 to 40 mesh is introduced into a laboratory scale reactor. The catalyst has a crystallinity in the range of 77 to 88%, 70% monoclinicity, an average crystallite size of 0.70 μm, a pore volume maxima at 3500 Å and Si/Al atomic ration of 91. The catalyst is heated under nitrogen flow to 200° C. overnight at ambient pressure to dry the catalyst. The nitrogen flow is discontinued and benzene with 10% mixed polyethylbenzenes is introduced to the reactor at a rate of 11.6 ml./min. The pressure is increased to 300 psig and the temperature allowed to equilibrate to 400° C. before introducing ethylene at a rate of 1 mole per 10 moles of benzene feed. The test is run for 8 days without interruption. During the test, diethylbenzene (DEB's) concentrations in the feed and effluent from the reactor are measured and the percentage of diethylbenzenes converted, based on the DEB concentration in the feed, is calculated. The results are set forth in Table 2 below:

TABLE 2

| Test Duration (days) | % DEB's Converted |
| --- | --- |
| 1.0 | 4.6 |
| 1.6 | 7.9 |
| 2.0 | 4.4 |
| 2.6 | 6.0 |
| 2.9 | 5.8 |
| 3.6 | 6.6 |

TABLE 2-continued

| Test Duration (days) | % DEB's Converted |
|---|---|
| 3.9 | 5.9 |
| 4.6 | 6.1 |
| 4.9 | 5.2 |
| 5.6 | 5.0 |
| 6.0 | 5.1 |
| 6.7 | 4.6 |
| 7.7 | 2.0 |

As can readily be observed by a comparison of the foregoing Examples, it is apparent that the use of an aluminosilicate catalyst having an average crystallite size of less than about 0.5 μm provides increased transalkylation activity.

EXAMPLE 2

This example is presented in two parts. The first part with the data presented in Table 3 is representative of the invention. In this part, twenty milliliters of an aluminosilicate catalyst is introduced into a laboratory scale reactor operated in a downflow mode. The catalyst has a crystallinity in the range of 76–93%, 70% monoclinicity, an average crystallite size of 0.40 microns, a maximum pore volume at a pore diameter for the binder of 3500 Angstroms and a Si/Al atomic ration of 114. The catalyst is heated under pressure to dry the catalyst. The nitrogen flow is discontinued and benzene is introduced to the reactor at a rate of 3.5 g/min. The pressure is increased to 300 psig and the temperature allowed to equilibrate at about 440° C. before introducing ethylene at a rate adjusted to 17.2% of the ethylbenzene flow. The space velocity is 70 hr$^{-1}$. The test is run for 120 days without interruption and the composition of the liquid product analyzed daily. A liquid product analysis giving an average composition is shown below:

TABLE 3

| Product | Wt. Percent |
|---|---|
| non-aromatic | 0.0505 |
| benzene | 80.3408 |
| toluene | 0.0219 |
| ethyl benzene | 17.7629 |
| p-xylene | 0.0076 |
| m-xylene | 0.0120 |
| cumene | 0.0206 |
| o-xylene | 0.0051 |
| n-propyl benzene | 0.0287 |
| p-ethyl toluene | 0.0024 |
| m-ethyl toluene | 0.0044 |
| t-butyl benzene | 0.0003 |
| iso-butyl benzene | 0.0055 |
| sec-butyl benzene | 0.0082 |
| styrene | 0.0051 |
| m-diethyl benzene | 0.9527 |
| p-diethyl benzene | 0.6438 |
| n-butyl benzene | 0.0110 |
| o-diethyl benzene | 0.0469 |
| heavies | 0.0697 |

A repeat run gave a heavies value of 0.0690 wt. percent.

In the second part of this example, the above procedure was repeated using a commercially available ZSM-5 type alkylation catalyst. An analysis of the resulting liquid product is shown below:

TABLE 4

| Product | Wt. Percent |
|---|---|
| non aromatic | 0.0473 |
| benzene | 80.7715 |
| toluene | 0.0302 |
| ethyl benzene | 17.1564 |
| p-xylene | 0.0063 |
| m-xylene | 0.0129 |
| cumene | 0.0200 |
| o-xylene | 0.0052 |
| n-propyl benzene | 0.0348 |
| p-ethyl toluene | 0.0031 |
| m-ethyl toluene | 0.0050 |
| t-butyl benzene | 0.0007 |
| iso-butyl benzene | 0.0064 |
| sec-butyl benzene | 0.0083 |
| styrene | 0.0043 |
| o-ethyl toluene | 0.0008 |
| m-diethyl benzene | 1.1789 |
| p-diethyl benzene | 0.5017 |
| n-butyl benzene | 0.0103 |
| o-diethyl benzene | 0.1011 |
| 1,2,3-trimethyl benzene | 0.0011 |
| heavies | 0.0937 |

Examination of Tables 3 and 4 shows a reduction in heavy residue production of around 30 percent, a commercially significant amount.

EXAMPLE 3

A plant alkylation unit having two reactors was used for the following test which was also presented in two parts. In the first part the catalyst of the present invention was loaded via standard sock loading procedures. The catalyst comprised extrudates with a "trilobe" shape having a nominal diameter of about 1/16" and a length of about 1/8–1/4". The catalyst has a crystallinity in the range of 76–93%, 70% monoclinicity, an average crystallite size of 0.40 microns, a maximum pore volume at a binder pore size of 3500 Angstroms and a Si/Al atomic ratio of 114. The average loaded density of the catalyst was 27.7 lb/ft$^3$.

After 30 days of operation at plant conditions in a single reactor mode, the catalyst was regenerated prematurely for experimental purposes. While the first reactor ran, the second reactor was loaded with the same type of catalyst. Once the second reactor was loaded and tested, the catalyst of the first reactor was again regenerated so that the catalyst could be evaluated in the parallel reactor mode with fresh catalyst in each reactor. Parallel operation at plant conditions was maintained for 60 days. The run was initiated at a reactor rate of 90% for both reactors, then increased to 92% on the twelfth day for the remainder of the test.

Figure 4:
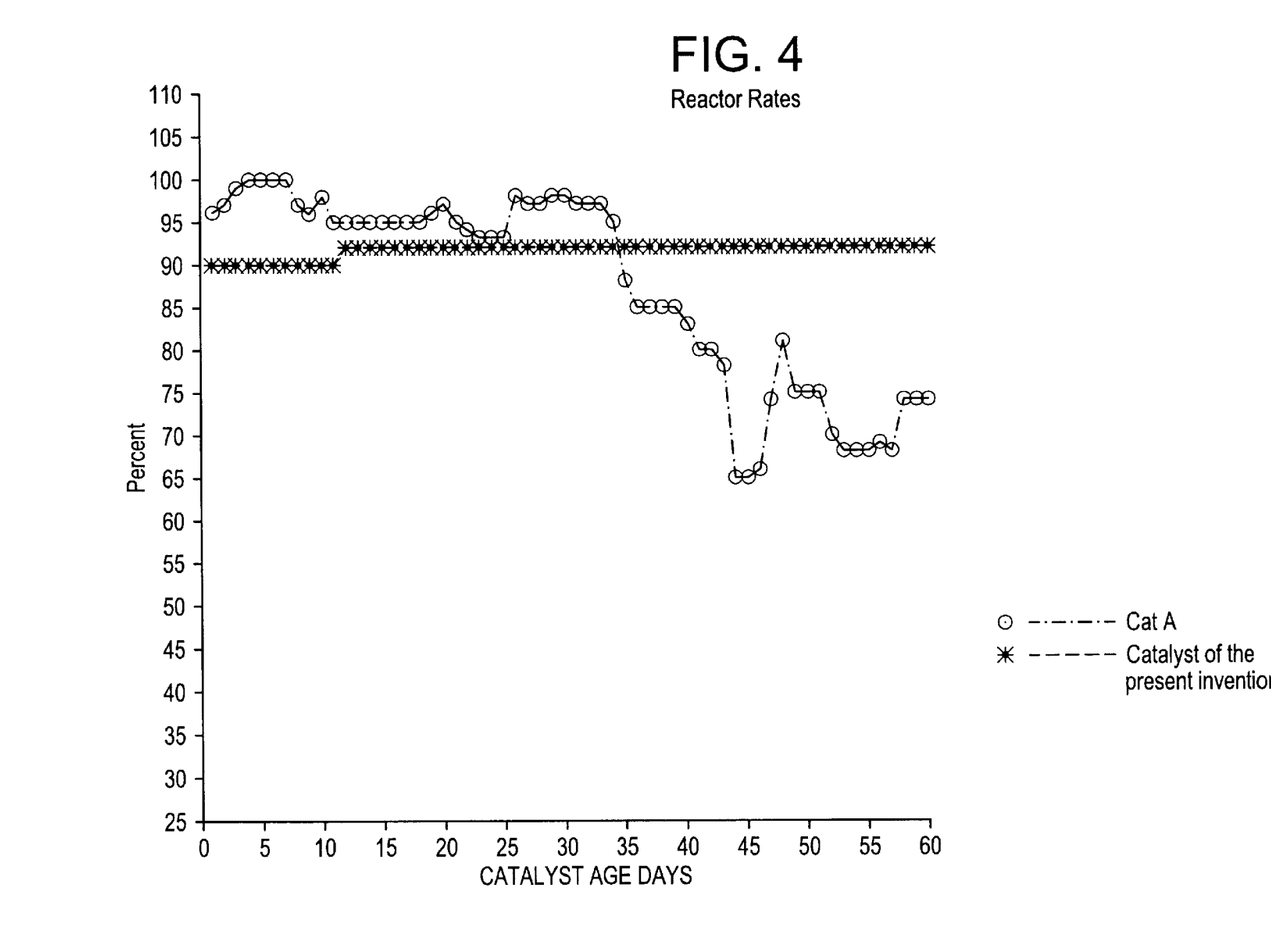
FIG. 4 is a comparison of the reactor rates of the plant runs of Comparative Example 3.

For the second part of this example, as a comparison, historical data for a ZSM-5 type commercial catalyst, Catalyst A was tabulated. It should be noted that the reactor rates were somewhat different, but the lower rates for Catalyst A should make the comparison to the results of the catalyst of the present invention conservative. A lower reactor rate generally provides more effective catalysis. A comparison of the two reactor rates over the catalyst life is seen in FIG. 4.

Figure 5:
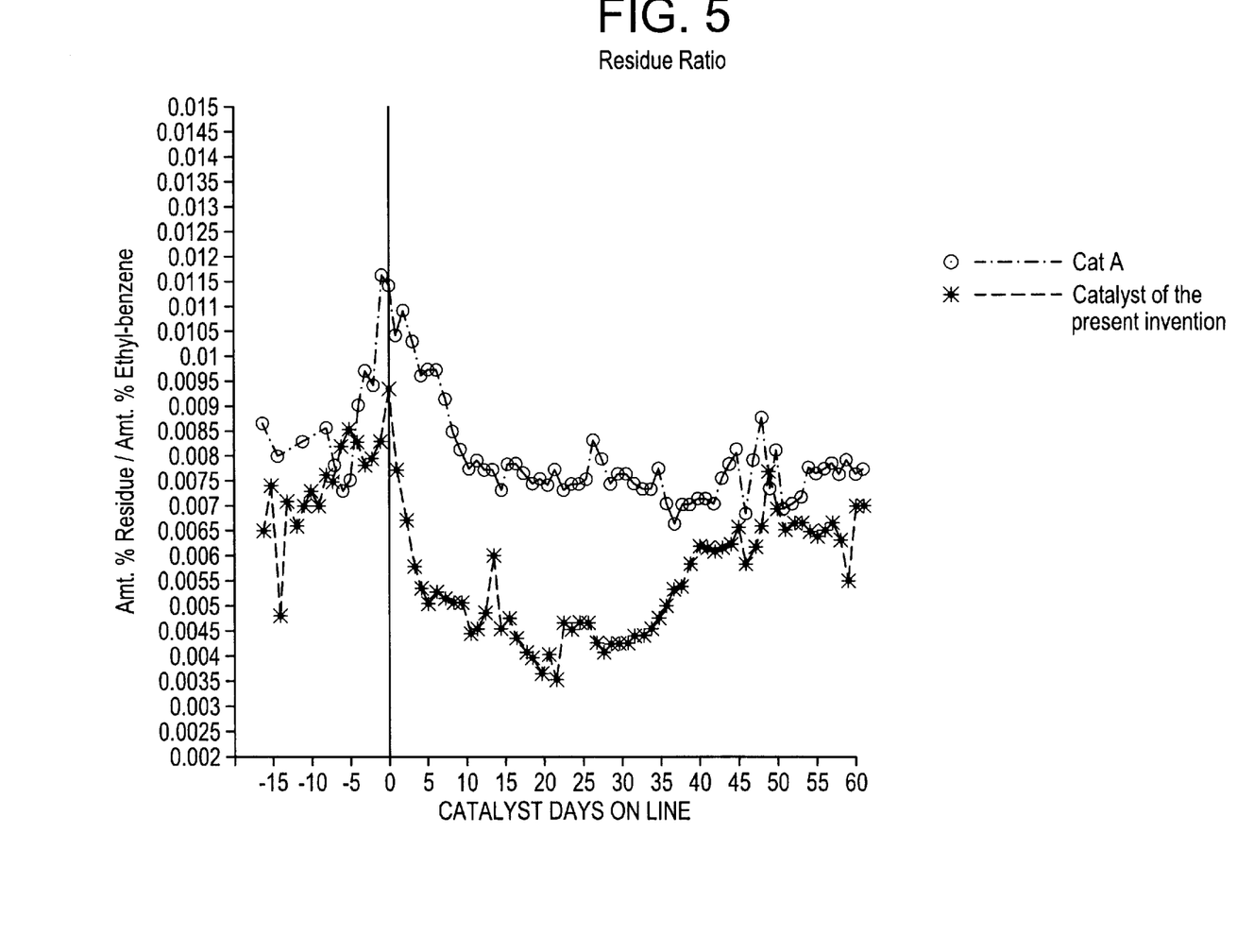
FIG. 5 is a graphical illustration of the ratio of the amount of heavy residue to the amount ethylbenzene, produced over the catalyst life for the two catalysts of Comparative Example 3.

FIG. 5 is a graphical representation of the amount of heavy aromatic compounds or heavy residue produced by the process of the present invention compared to that produced by Catalyst A. The composition of the residue streams associated with the two catalysts is seen in Table 5, below.

TABLE 5

| Catalyst, Invention | Catalyst A | Stream Component |
|---|---|---|
| 20.988 wt. % | 15.359 wt. % | Napthalene & lighter |
| 34.196 | 30.881 | Diphenylmethane |
| 10.296 | 17.602 | 1,1-Diphenylethane |
| 8.517 | 10.494 | 1,2-Diephenylethane |
| 24.973 | 24.694 | Heavies |

For comparison, the compositions of the recycle streams are shown in Table 6.

TABLE 6

| Catalyst, Invention | Catalyst A | Stream Component |
|---|---|---|
| 4.21 wt. % | 5.35 wt. % | ethylbenzene |
| 637 ppm | 858 ppm | xylenes |
| 14.65 wt. % | 13.19 wt. % | cumene |
| 22.36 wt. % | 20.02 wt. % | n-propylbenzene |
| 0.62 wt. % | 0.74 wt. % | ethyltoluene |
| 5.54 wt. % | 5.06 wt. % | butylbenzene |
| 1.40 wt. % | 1.17 wt. % | trimethylbenzene |
| 684 ppm | 923 ppm | styrene |
| 42.82 | 44.96 | diethylbenzene |
| 7.24 | 8.36 | heavies |

It can be clearly seen from FIG. 5 that significantly less residue is produced by the process using the catalyst of the present invention than by Catalyst A. Table 5 shows a notable shift in composition of the heavy residue stream produced by the catalyst of the present invention toward the lighter multi-ring compounds. Conversely, the heavy residue stream from the Catalyst A process contains more diphenylethanes. The streams from the two catalysts contain about equivalent amounts of heavy components. The composition of the recycle streams from the two processes are also shown in Table 6.

Having described specific embodiments of the present invention, it will be understood that modifications thereof may be suggested to those skilled in the art, and it is intended to cover all such modifications as fall within the scope of the appended claims.

We claim:

1. An alkylation process comprising the steps of:
   reacting a mixture of an aromatic hydrocarbon and an alkylation agent in an alkylation zone containing a silicalite molecular seive catalyst of predominantly monoclinic symmetry having a Si/Al atomic ratio of 50–500 and an average crystallite size of no more than about 0.5 microns under conversion conditions to produce in alkylated aromatic hydrocarbon stream;
   separating unreacted aromatic hydrocarbon from the alkylated aromatic hydrocarbon stream;
   recovering alkylated aromatic hydrocarbon from the alkylated aromatic hydrocarbon stream to leave a remainder stream;
   separating the remainder stream into a first residual hydrocarbon stream and a second residual hydrocarbon stream; and
   purging the second residual stream, wherein the second residual stream comprises less than 0.8 weight percent of the alkylated aromatic hydrocarbon stream based on the weight of the alkylated aromatic hydrocarbon.

2. The process of claim 1 wherein the conversion conditions include a temperature of from about 250° C. to about 500° C. and a pressure of from about 200 psi to about 500 psi.

3. The process of claim 1 wherein the aromatic hydrocarbon is benzene and the alkylation agent is ethylene and wherein benzene is alkylated with ethylene to produce ethylbenzene.

4. The process of claim 3 wherein the molar ratio of benzene to ethylene in the alkylation zone is from about 2:1 to about 20:1.

5. The process of claim 1 wherein the catalyst contains less than about 50 ppm sodium.

6. The process of claim 1 wherein the weight percent of the second residual stream is less than 0.5 weight percent of the alkylated aromatic stream based on the weight of the alkylated aromatic hydrocarbon.

7. The process of claim 1 further comprising the step of transalkylating the first residual hydrocarbon stream.

8. The process of claim 7 wherein the transalkylation step takes place in the alkylation zone.

9. The process of claim 7 wherein the transalkylation step takes place in a separate transalkylation unit.

10. The process of claim 1 wherein the size of 90% of the crystallites is less than 0.70 microns.

11. The process of claim 1 wherein the catalyst has a maximum pore size in the range from about 1000 to 4000 Angstroms.

12. The process of claim 1 wherein the catalyst has a maximum pore size in the range from about 1000 to 1800 Angstroms.

13. The process of claim 1 wherein the catalyst has a Si/Al atomic ratio of 100–200.

14. The process of claim 1 further comprising the step of recycling the unreacted aromatic hydrocarbon to the alkylation zone.

15. An alkylation process comprising the steps of:
   reacting a mixture of benzene and polyalkylbenzenes with ethylene in an alkylation zone to produce an alkylated aromatic stream containing ethylbenzene over a silicalite molecular sieve catalyst of predominantly monoclinic symmetry having a Si/Al atomic ratio in the range between 50 and 150, and average crystallite size of no more than about 0.5 microns, and a sodium content of less than about 50 ppm, and wherein the size of about 90% of the crystallites is less than 0.70 microns and wherein the molar ratio of benzene to the ethylene is about 2:1 to 20:1;
   separating unreacted benzene from the alkylated aromatic stream;
   recovering ethylbenzene from the alkylated aromatic stream to leave a remainder stream;
   separating the remainder stream into a first residual stream and a second residual stream;
   recycling the unreacted benzene to the alkylation zone; and
   purging the second residual stream, wherein the second residual stream comprises less than 0.8 weight percent of the alkylated aromatic stream based on the weight of ethylbenzene.

16. The process of claim 14 wherein the conversion conditions include a temperature of from about 250° C. to about 500° C. and a pressure of from about 200 psi to about 500 psi.

17. The process of claim 14 wherein the weight of the second residual stream comprises less than 0.5% of the alkylated hydrocarbon stream based on the weight of ethylbenzene.

18. The process of claim 14 further comprising the step of transalkylating the first residual stream.

19. The process of claim 17 wherein the transalkylation step takes place in the alkylation zone.

20. The process of claim 17 wherein the transalkylation step takes place in a separate transalkylation unit.

21. The process of claim 14 wherein the catalyst has a maximum pore volume at a pore size in the range of 1000 to 4000 Angstroms.

22. The process of claim 14 wherein the catalyst has a maximum pore size in the range from about 1000 to 1800 Angstroms.

23. The process of claim 14 wherein the catalyst has a Si/Al ratio of 100 to 200.

* * * * *